(12) United States Patent
Hoornaert et al.

(10) Patent No.: US 10,314,554 B2
(45) Date of Patent: Jun. 11, 2019

(54) MEDICAL IMAGING SYSTEM CAPABLE OF PREVENTING UNINTENDED X-RAY RADIATION TO AN OBJECT

(71) Applicant: KONINKLIJKE PHILIPS N.V., Eindhoven (NL)

(72) Inventors: Bart Pierre Antoine Jozef Hoornaert, Eindhoven (NL); Eugene Alekseyevich Ivanov, Eindhoven (NL); Johan Juliana Dries, Eindhoven (NL); Raoul Florent, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 305 days.

(21) Appl. No.: 15/122,790

(22) PCT Filed: Feb. 17, 2015

(86) PCT No.: PCT/EP2015/053262
§ 371 (c)(1),
(2) Date: Aug. 31, 2016

(87) PCT Pub. No.: WO2015/132069
PCT Pub. Date: Sep. 11, 2015

(65) Prior Publication Data
US 2017/0071558 A1    Mar. 16, 2017

(30) Foreign Application Priority Data
Mar. 4, 2014   (EP) .................... 14305304

(51) Int. Cl.
*A61B 6/00*    (2006.01)
*A61B 6/10*    (2006.01)
*A61B 6/06*    (2006.01)

(52) U.S. Cl.
CPC ............... *A61B 6/107* (2013.01); *A61B 6/06* (2013.01); *A61B 6/4233* (2013.01);
(Continued)

(58) Field of Classification Search
CPC ......... A61B 6/06; A61B 6/107; A61B 6/4233; A61B 6/4441; A61B 6/4464; A61B 6/5264; A61B 6/54; A61B 6/542
See application file for complete search history.

(56) References Cited

U.S. PATENT DOCUMENTS 6,435,717 B1   8/2002  Kohler
7,016,453 B2   3/2006  Ruimi
(Continued)

FOREIGN PATENT DOCUMENTS

DE   102007003876 B3   7/2008
DE   102011080607 A1   2/2013
(Continued)

*Primary Examiner* — Dani Fox

(57) ABSTRACT

A medical imaging system having an X-ray image acquisition device, a plurality of proximity sensors located at components of the X-ray image acquisition device and a processing unit is able to prevent unintended X-ray radiation to an object in a field of irradiation. For this purpose, the processing unit is configured for determining temporal differences of distance information delivered by the proximity sensors, for generating reference distance information based on acquired distance information with an X-ray source, an X-ray detector and the patient support in fixed positions, for filtering out reference distance information from the acquired distance information and for generating a signal in case temporal differences are determined exceeding a predetermined threshold.

14 Claims, 2 Drawing Sheets

(52) U.S. Cl.
CPC .......... *A61B 6/4441* (2013.01); *A61B 6/4464* (2013.01); *A61B 6/54* (2013.01); *A61B 6/542* (2013.01); *A61B 6/5264* (2013.01)

(56) References Cited

U.S. PATENT DOCUMENTS

| | | |
|---|---|---|
| 7,290,930 B2 | 11/2007 | Hoheisel |
| 7,570,064 B2 | 8/2009 | Roziere |
| 2004/0125918 A1 | 7/2004 | Shanmugavel |
| 2008/0279333 A1* | 11/2008 | Sattler .................... A61B 6/102 378/98.2 |

FOREIGN PATENT DOCUMENTS

| | | |
|---|---|---|
| JP | 2006034354 A | 2/2006 |
| WO | 2002085212 A2 | 10/2002 |
| WO | 2006025000 A1 | 3/2006 |

* cited by examiner

MEDICAL IMAGING SYSTEM CAPABLE OF PREVENTING UNINTENDED X-RAY RADIATION TO AN OBJECT

CROSS-REFERENCE TO PRIOR APPLICATIONS

This application is the U.S. National Phase application under 35 U.S.C. § 371 of International Application No. PCT/EP2015/05362, filed on Feb. 17, 2015, which claims the benefit of European Patent Application No. 143053049.9, filed on Mar. 4, 2014. These applications are hereby incorporated by reference herein.

FIELD OF THE INVENTION

The invention relates to a medical imaging system capable of preventing unintended X-ray radiation to an object and to a method for preventing unintended X-ray radiation in such a medical imaging system.

BACKGROUND OF THE INVENTION

During interventional X-ray procedures, an interventionist should avoid placing his/her hands into the direct X-ray beam. However, in many cases, or linked to the clinical task to be conducted, this may be unavoidable. Several countermeasures are known, for example the use of gloves containing an X-ray impermeable material such as lead, the use of a smooth cream for attenuating X-rays, the use of ring-finger attachable dosimeters, etc.

Furthermore, it is known to use an X-ray device having an X-ray source and an X-ray detector as well as indicator means for illuminating an irradiation field traversed by X-rays, which is situated over a patient and between the X-ray detector and the patient. Indicator means are provided for monitoring the irradiation field. Thereby, the operator's hand may be detected when placed in the X-ray beam, such that alarming means give notice that a hand is irradiated. For example, this may be gathered from EP 1 084 678 A1.

US 2008/0279333 A1 discloses a C-arm X-ray imaging system that is provided with proximity sensors. Prior to an examination, the proximity sensors scan real outer dimensions of a patient as an individual 'static envelope'. During the examination, the real outer dimensions of the patient are determined in real-time as the 'dynamic envelope'. The static and dynamic envelopes are compared and, if the 'distance' between individual static and dynamic envelopes exceeds an adjustable value, a movement of the C-arm or the patient table may be stopped.

SUMMARY OF THE INVENTION

It may be advantageous to provide a medical imaging system comprising an X-ray source and an X-ray detector, which medical imaging system is able to prevent the irradiation of a hand by a direct X-ray beam as much as possible, without requiring any manual input. In the following, such a medical imaging system is proposed, which comprises the features of independent claim 1. Advantageous embodiments and further improvements may be gathered from the sub-claims and the following description.

The medical imaging system according to the invention comprises an X-ray image acquisition device having an X-ray source and an X-ray detector, a patient support positionable between the X-ray source and the X-ray detector, a plurality of proximity sensors located at at least one of housing of at least one of the X-ray source and the X-ray detector and a processing unit couplable with the plurality of proximity sensors. The plurality of proximity sensors is configured for acquiring distance information for an imaging region between the X-ray detector and the X-ray source. The processing unit is configured for generating reference distance information from distance information acquired without an object to be protected from unintended irradiation being present in the imaging region, and for detecting a presence of said object in the imaging region by means of determining a temporal difference between actual distance information and the reference distance information, and for generating a warning signal if the temporal difference exceeds a predetermined threshold.

The medical imaging system above may be an apparatus for medical diagnosis and/or therapy, which is based on providing X-ray image acquisition by means of an X-ray source and an X-ray detector. For example, the X-ray image acquisition device may be of a C-arm type having a C-shaped frame with two opposed ends facing each other, wherein one end carries the X-ray source and wherein the opposite end carries the X-ray detector, which may be a flat-panel detector. The C-shaped frame may be rotated about all three reference axes around the patient and may be moved along these axes relative to the patient, which is locatable on the patient support positionable between the X-ray source and the X-ray detector.

The latter may exemplarily be a table, on which a patient may lie flat. Especially for interventional use, the geometry of the X-ray image acquisition device may be altered relative to the patient to be examined. This includes movement of the X-ray image acquisition device, e.g. rotation, angulation, lateral or horizontal position, as well as movement of the patient support, e.g. its height, longitudinal or transversal position, etc. Also, the alignment of the X-ray source and/or the X-ray detector may be altered, leading to varying a source-image-distance, rotating the detector, etc.

The processing unit may comprise or may be coupled with a memory unit and is configured for executing algorithms that allow determining the temporal differences in the distance information. For this purpose, the memory unit may store the reference distance information and/or the predetermined threshold.

A proximity sensor in the meaning of claim 1 may be any sensor which is capable of detecting the distance to an object in the proximity of the sensor and for generating a signal depending on the actual proximity of the object. The plurality of proximity sensors may be arranged in a predetermined pattern, which may at least include rows and matrices of proximity sensors. While each proximity sensor delivers a distance signal, which depends on the proximity of any object facing the respective proximity sensor, the plurality of proximity sensors deliver a data field having a set of distance information. This data field, wherein field is to be considered a set of a plurality of values, is comparable to an image, while instead of brightness and color information, distance information are given. These data fields may therefore also be referred to as "distance images".

The proximity sensors are preferably attached to or integrated into a housing of the respective one of the X-ray source or X-ray detector, which also includes an arrangement directly in front of the X-ray source facing the X-ray detector and vice versa.

Temporal differences of distance information are determined by receiving distance information from the proximity sensors and determining the difference between two sets of distance information through element-wise subtraction of the distance information values from each proximity sensor in the respective data fields, i.e. the distance images. The two sets of distance information do not need to be consecutive sets but more particular refer to a set of reference distance information and a set of actual distance information, the latter being distance information acquired during imaging of a patient, preferably during an interventional X-ray procedure.

A gist of the invention therefore lies in that the processing unit, which is coupled to the plurality of proximity sensors, generates distance images, which are investigated for detecting sudden inhomogeneities that occur in the actual distance information which may be interpreted as being caused by an object, such as a hand or other body part of an interventionist, entering, or being present in, the imaging region during an interventional procedure. When such event is detected, i.e. when the temporal difference between the actual and reference distance information exceeds the predetermined threshold, a warning signal may be generated that enables the system and/or the physician to take appropriate measures for protecting such object from undesired irradiation with X-rays.

The above-mentioned reference distance information represents a patient to be examined positioned on the patient support as explained above. If neither the X-ray image acquisition device nor the patient support is moved, the distance information acquired by the plurality of distance sensors may be considered steady. However, there may still be slight movements due to the breathing of the patient, etc.

Given the fact that a disturbance in the acquired distance information by a hand or other body part of the interventionist reaching the imaging region between X-ray source and X-ray detector distinctly differs from such slight patient movements, this event is well detectable. The processing unit therefore filters out the reference distance information from the actual distance information continuously, in order to identify more distinct motions. In this context, the expression filtering may be understood as subtracting, i.e. for determining the difference between the actual and the reference distance information.

The warning signal generated by the processing unit in case an object is detected in the monitored space, which may equal to or exceed the irradiation field, allows to provide countermeasures for preventing an irradiation of the interventionist's hand or other body part, to initiate a warning provider, which may be an optical or acoustic warning provider. These countermeasures are mentioned further below.

In a preferred embodiment, the processing unit is configured for defining a tolerance range corresponding to changes in acquired distance information due to movements of a patient on the patient support during an intervention. As indicated above, these slight movements are for example caused by breathing of the patient.

The tolerance range may be determined by investigating, i.e. monitoring and assessing, the level of movement of the respective patient over a short period of time. This period of time does not need to be strictly limited, as the proximity sensors do not provide any harmful X-ray emission. It is therefore not only possible to conduct the generation of reference distance information over some seconds, but also over a period of time in the order of a minute or even longer.

Generating the reference distance information may be conducted through a large number of different methods. For example, slight distance information deviations may be monitored for a certain period of time while it should be guaranteed that no other object enters the space between X-ray source and X-ray detector. It may then be possible to define certain reference threshold values, which represent appropriate boundary conditions for the distance information caused by the patient's motion. Alternatively or additionally, the tolerance range is provided by means of creating a physical model of the patient, in which the breathing motion, etc. of the patient are simulated. In either case, the predetermined threshold for the processing unit to generate a warning signal may be set outside the defined tolerance range, which advantageously enables the processing unit to distinguish between normal patient movements and an object, such as a physician's hand, entering the imaging region in a reliable manner.

In a preferred embodiment, the proximity sensors are realized as capacitive sensors, which comprise a sensing electrode, which has a surface with electroconductive areas and non-electroconductive areas, wherein the proximity sensors adapted for measuring an electrical field between the sensing electrode and an object. Such a proximity sensor may comprise a rather flat shape, which allows to easily integrate the proximity sensors into a component of the X-ray image acquisition device. Further, by choosing a low thickness of the electrodes, X-ray beams are hardly influenced or attenuated.

Still further, the proximity sensors may be arranged in a matrix, which may exemplarily be rectangular. Based on the signals delivered by the proximity sensors, a data field, i.e. distance information, can be created through setting up a matrix filled by distance values, which are correlated with the proximity sensors arranged in the same positions of the matrix.

Advantageously, the medical imaging system may be configured for interrupting the emission of X-ray radiation from the X-ray source if the processing unit generates the warning signal. For example, in case the processing unit detects a hand of an operator or any other object reaching the field of irradiation, interrupting the X-ray emission is a quick solution for preventing unintended irradiation of the hand. As stated earlier, the monitored space, from which the "distance images" are created, may be larger than the field of irradiation such that the operator's hand may already be detected clearly before it enters the field of irradiation.

In a still further embodiment, the medical imaging system may comprise beam restricting devices located at the X-ray source, which are adapted for shaping the field of irradiation by means of wedges and/or collimating devices. In case a warning signal is generated by the processing unit, the beam restricting devices may be controlled such that the field of irradiation excludes a portion of the imaging region where the object is present. In other words, if in the "distance image" an object such as an approaching hand is recognized, this region may be a desired destination for moving the collimating device or the wedge.

In this regard, the processing unit is configured for locating an object approaching into the field of irradiation through identification of at least one affected proximity sensor of the plurality of proximity sensors that is exposed to a temporal difference that exceeds the predetermined threshold. This means, that not only the fact that an operator's hand is approaching the field of irradiation, but also the location of its approach can be detected to provide for sufficient countermeasures.

The medical imaging system may furthermore comprise a warning provider, which may be an optical or acoustical warning provider operable at least temporarily if a warning signal is generated by the processing unit. The operation may be temporary and may be integrated into a user interface, a viewing device or any other means integrated into the medical imaging system that is constantly observed by the operator during its operation.

Still further, the processing unit may be adapted for regenerating the reference distance information after a component of the X-ray image acquisition device and/or the patient support has been moved. It is thereby possible to automatically adjust the warning function during an interventional process, which usually includes motion of the X-ray image acquisition device.

Still further, distance information may be gathered so that not only the imaging region itself is considered, but also an adjacent area which represents a safety zone. Thereby, also scatter of X-ray radiation may be sufficiently considered, as hands in the safety zone just outside the imaging region may also be exposed to a relatively high amount of X-ray dose. Determining such a safety zone may be more complex than just adding a fixed unidirectional safety zone to the imaging region, for example anatomical models that represent three-dimensional scatter effects may be established and used. This anatomical model may also be used for creating the reference data, as stated above.

In this context it is indicated that the accuracy, directional specificity and sensitivity of the proximity sensors will have impact on the quality and accuracy of the corrective/awareness actions. Means to overrule the system actions may be included into the medical imaging system.

The invention also relates to a method for preventing unintended X-ray radiation in a medical imaging system as described above, the method having the features according to the independent method claim.

The method thus comprises generating X-ray beams through an X-ray source of an X-ray image acquisition device in direction of an X-ray detector of the X-ray image acquisition device, between which X-ray source and X-ray detector a patient support is positionable; acquiring, from of a plurality of proximity sensors located at at least one of the X-ray source and the X-ray detector, distance information for an imaging region between the X-ray source and the X-ray detector; generating reference distance information from distance information acquired without an object to be protected from unintended irradiation being present in the imaging region; determining a temporal difference between actual distance information and the generated reference distance information, and generating a warning signal if the temporal difference exceeds a predetermined threshold.

The structural relationships of the elements mentioned regarding the method may be gathered from the above description of the medical imaging system, as well as the generation of the predetermined reference distance information.

Furthermore, the method may comprise interrupting the emission of X-ray radiation from the X-ray source if the warning signal is generated. Alternatively or additionally, the method may further comprise selectively controlling at least one beam restricting device upon generation of the warning signal to shape a field of irradiation between the X-ray source and the X-ray detector. Preferably, the method also comprises locating an object approaching into the field of irradiation through identification of at least one affected proximity sensor that is exposed to a temporal difference that exceeds the predetermined threshold.

These and other aspects of the present invention will become apparent from and be elucidated with reference to the embodiments described hereinafter.

DETAILED DESCRIPTION OF EMBODIMENTS

Figure 1:
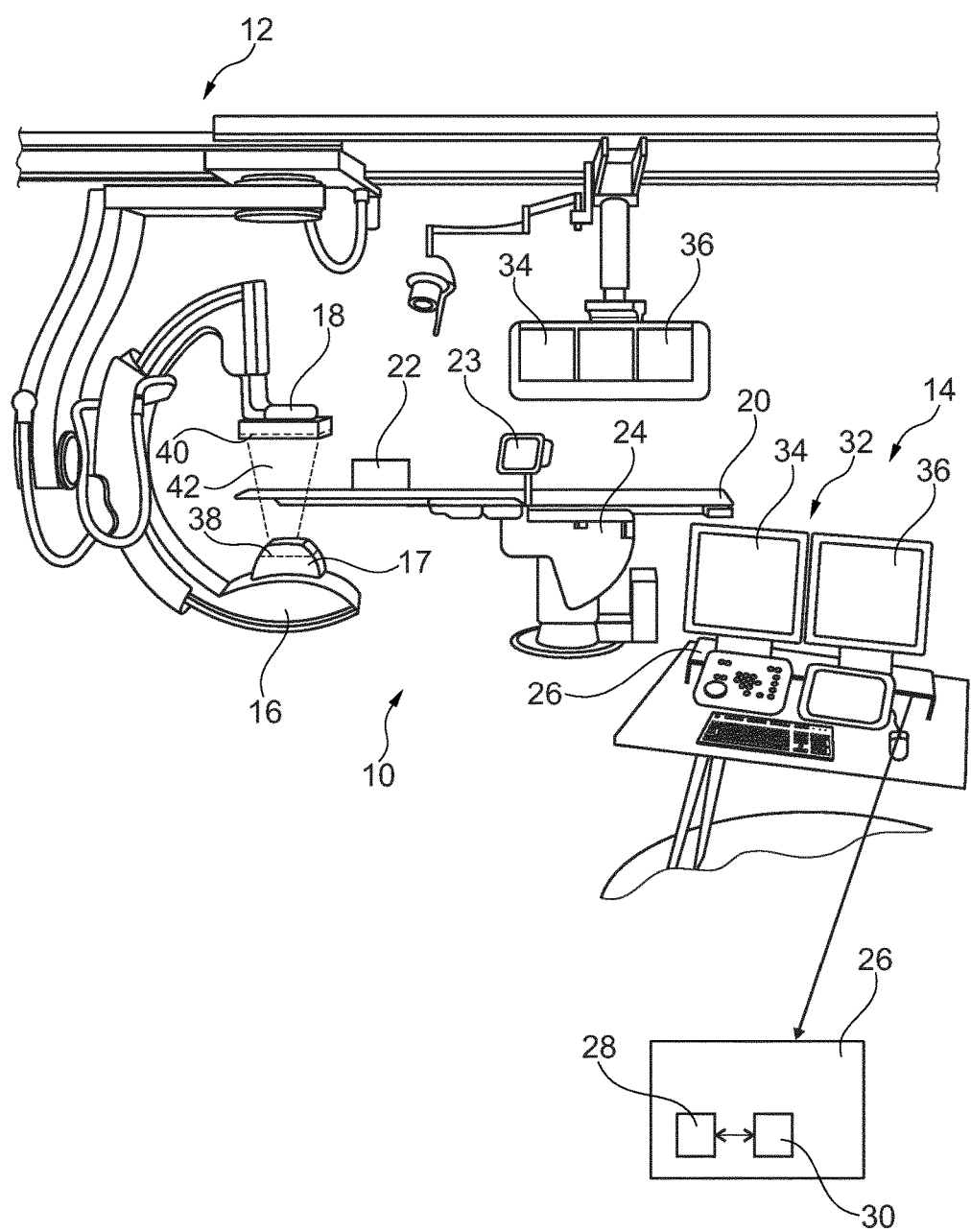
FIG. 1 shows a medical imaging system in a schematic overview.

According to the example of FIG. 1, a medical imaging system 10 is provided, comprising an X-ray image acquisition device 12, and exemplarily an interventional image viewing device 14, which comprises or constitutes a user interface means.

The X-ray image acquisition device 12 comprises an X-ray source 16, a beam restricting device 17 and an X-ray detector 18. The X-ray image acquisition device 12 is configured to provide X-ray images of an object, i.e. a patient. Further, a support table 20, for example for receiving/holding an object, such as a patient, is shown, who may receive a contrast agent from a contrast agent injector 22 for introducing a contrast agent into vessels of a patient during the intervention.

A control unit 24 may be present to control the X-ray image acquisition device 12, i.e. the position and orientation, as well as the position and orientation of the support table 20. However, a control unit 24 may be also be distributed over several locations through different components, which are coupled with each other to provide the required functions.

It should be noted that the X-ray image acquisition device 12 shown in FIG. 1 is exemplarily chosen as a C-arm structure. However, also other X-ray image acquisition devices, movable or non-movable, may be used without departing from the concept of the invention, as the medical viewing system 10 is particularly able to prevent unintended X-ray radiation of an object, e.g. an operator's hand, irrespective of the kind of medical viewing system of X-ray image acquisition device.

The interventional image viewing device 14 exemplarily comprises a calculation unit 26, which inter alia includes an image data providing unit 28 and a processing unit 30. The interventional image viewing device 14 also comprises a display unit 32 with a first display 34 and a second display 36, which may also be found at the X-ray image acquisition device 12 for providing X-ray images and processed images, such as a visualization image created by the processing unit 30. If desired, also distance images may be depicted, which are explained further below.

The image data providing unit 28 is exemplarily configured to provide interventional images of a region of interest of an object showing a certain vasculature, such as an aorta.

As indicated by dashed lines, a first matrix of a plurality of proximity sensors 38 is arranged at the X-ray source 16, while exemplarily also a second matrix of proximity sensors 40 is arranged at the X-ray detector 18. Since the orientation of the C-arm structure depends on the operator's task, it cannot be excluded that the object to be protected from unwanted X-ray radiation, e.g. an operator's hand, may reach the imaging region 42 in an area between the detector 18 and the patient on the table 20 or, with another orientation of the C-arm structure, the imaging region 42 in an area between the X-ray source 16 and the patient. Therefore, in this example, both X-ray source 16 and X-ray detector 18 advantageously comprise such a plurality of proximity sensors. However, this is not necessary and it may also be advantageous to provide only a first matrix of a plurality of proximity sensors 38 at the X-ray source 16 or only a second matrix of a plurality of proximity sensors 40 at the X-ray detector 18.

The matrices of proximity sensors 38, 40 may each be of a rectangular shape, which leads to the ability to provide rectangular "distance images". These contain acquired distance information, which are correlated with the respective proximity sensor position in the respective matrix. This may lead to a representation shown in FIG. 2 explained further below.

The processing unit 30 should be configured for determining temporal differences between actual distance information acquired through a plurality of proximity sensors 38, 40 and reference distance information. These may preferably be based on acquired distance information with the X-ray source 16, the X-ray detector 18 and the table 20 in fixed positions. By determining the difference between actual distance information and the reference distance information, the latter are filtered out from the acquired distance information. The processing unit (30) is furthermore configured for generating a warning signal in case the determined temporal differences are exceed a predetermined threshold. The processing unit hence may reliably and quickly determine the approach of an object into the imaging region 42, which event clearly differs from ordinary movements of the patient on the table 20, in order to generate the warning signal.

For this purpose, the processing unit 30 may comprise a memory for storing acquired distance information of at least one certain point of time to provide for a basis to create reference distance information, which resemble the mean distances of the patient to be examined for the proximity sensors acquired in the past, and to filter our reference distance information from acquired actual distance information.

The warning signal may lead to a plurality of different actions. For example, the beam restricting device 17 may shape the field of irradiation such that a part of the imaging region 42, in which the object is detected, is excluded from X-ray radiation. Alternatively or additionally thereto, it may also be possible to provide a warning through a warning provider, which may be integrated into the interventional viewing device 14 and is adapted for raising the operator's awareness of a detected object in the field of irradiation. This may be an optical and/or an acoustical warning.

Still further, the processing unit 30 may be used for controlling the X-ray source 16, so as to interrupt the emission of X-ray radiation from the X-ray source 16. Thus, once the warning signal is generated, X-ray radiation will not be provided until the detected object has been removed from the imaging region 42.

The processing unit 30 may be coupled to a user interface, which may be included in, coupled with or constituted by the image viewing device 14. However, the user interface and/or a human interface device may also be supported by a further screen 23 located in the vicinity of the table 20 and configured for receiving user input and/or showing information. For example, the screen 23 may be a touch screen module providing virtual buttons for operating/controlling the medical imaging system 10 and may also comprise means for raising the operator's awareness if a warning signal is generated.

Figure 2:
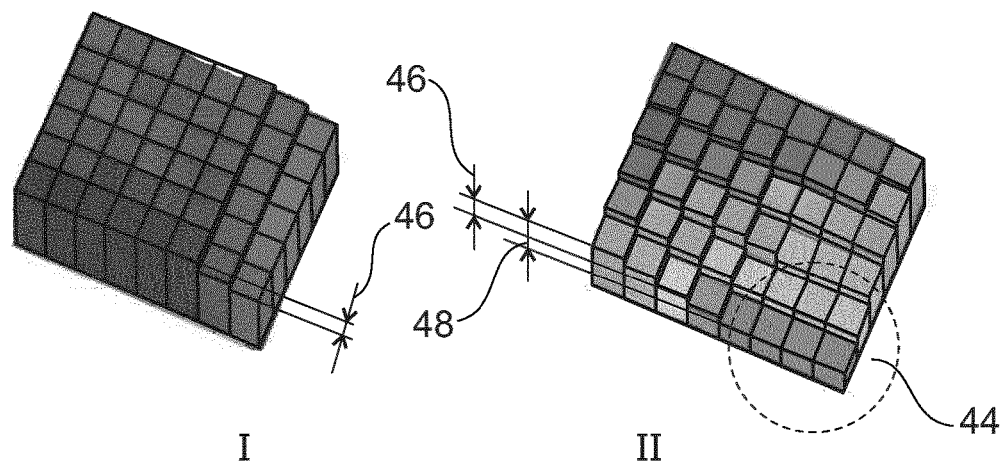
FIG. 2 shows different distance images, a reference distance image and a distance image showing an object in the irradiation field.

FIG. 2 shows two different "distance images" I and II in form of bar graphs, wherein the height of the individual bars correlate to the acquired distances, while the shading/brightness of each graph is correlated with the height of the bars. Hence, long bars stand for a larger distance than short bars.

Distance image I, which is situated on the left, may represent the reference distance information. Here, all distances measured at the respective proximity sensor positions are rather large and comprise almost the same shading. This may be related to the reference distance information, in which the operator's hand is not present in the imaging region and, thus, not in the vicinity of the respective proximity sensors. The patient on the table of the medical imaging system will usually move slightly during an intervention or procedure, such slight motions should therefore be neglected. A simple approach to consider this slight motion may be to define a certain neglectable distance difference 46 or movement tolerance range, which resembles the difference between the boundaries of the permanently changing acquired distances to the patient. Hence, this neglectable distance is a part of the determined reference distance information.

However, distance image II, which is situated on the right, shows a region 44, in which distance information drastically distinguishes from the remaining areas and distance image I. For example a distance 48 may be measured between an object and remaining parts of the distance image II. The distance 48 clearly distinguishes from the above mentioned neglectable distance 46. This results from a clearly reduced detected distance of an object, i.e. the operator's hand, in the vicinity of the X-ray source 16 or the X-ray detector 18.

The reference distance information may be filtered out from the actual distance image II, which may be conducted through subtracting the individual distance values, i.e. the height of the bars, from the distance values of the distance image II. If no object is placed in the field of irradiation, the filtered result would not show any detected distance or just (weak) noise.

However, as it is clearly apparent from distance image II, in a section 44 distance information is present, which clearly differs from the reference distance information. Hence, a warning signal is to be generated.

Figure 3:
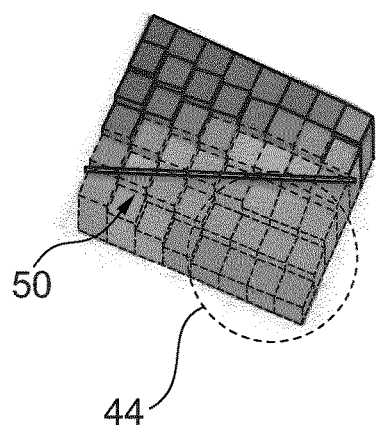
FIG. 3 shows a movement of a beam restricting device upon detection of an object in the irradiation field.

FIG. 3 shows a possible countermeasure for preventing unintended irradiation on the object, i.e. the operator's hand. Here, a wedge 50 may be used for limiting the irradiation in section 44. Through identification of those proximity sensors, which are exposed to the object distances clearly exceeding the predetermined threshold, the desired position for moving a beam restricting device 50 in form of a wedge can be determined. The processing unit 30 may move the beam restricting device 50 into this section upon generating the warning signal.

In another exemplary embodiment of the present invention, a computer program or a computer program element is provided that is characterized by being adapted to execute the method steps of the method according to one of the preceding embodiments, on an appropriate system.

The computer program element may therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

10 Medical viewing system
12 X-ray image acquisition device
14 Image viewing device
16 X-ray source
17 Beam restricting device
18 X-ray detector
20 Support table (patient support)
22 Contrast agent injector
23 Screen
24 Control unit
26 Calculation unit
28 Data providing unit
30 Processing unit
32 Display unit
34 First display
36 Second display
38 Plurality of proximity sensors
40 Plurality of proximity sensors
42 Imaging region
44 Section of the field of irradiation
46 Neglectable distance (reference distance)
48 Distance exceeding the neglectable distance
50 Beam restricting device

The invention claimed is:

1. A medical imaging system, comprising:
an X-ray image acquisition device having an X-ray source and an X-ray detector,
a patient support positionable between the X-ray source and the X-ray detector,
a plurality of proximity sensors located at at least one of the X-ray source and the X-ray detector, and
a processing unit couplable with the plurality of proximity sensors,
wherein the plurality of proximity sensors is configured for acquiring distance information for an imaging region between the X-ray detector and the X-ray source,
wherein the processing unit is configured for generating reference distance information from distance information acquired without an object to be protected from unintended irradiation being present in the imaging region, and
wherein the processing unit is further configured to detect a presence of said object in the imaging region by means of determining a temporal difference between actual distance information and the reference distance information, and for generating a warning signal if the temporal difference exceeds a predetermined threshold, the predetermined threshold being set outside a defined tolerance range representing boundary conditions for the distance information caused by patient movements, so as to distinguish between said patient movements and the presence of the object to be protected from unintended irradiation in the imaging region.

2. The medical imaging system of claim 1,
wherein the processing unit is additionally configured to define a tolerance range corresponding to changes in acquired distance information due to movements of a patient on the patient support during an intervention.

3. The medical imaging system of claim 1,
wherein the proximity sensors are arranged in a matrix.

4. The medical imaging system of claim 1,
wherein the medical imaging system is configured for interrupting the emission of X-ray radiation from the X-ray source if the processing unit generates said warning signal.

5. The medical imaging system of claim 1,
further comprising at least one beam restricting device located at the X-ray source adapted for shaping a field of irradiation between the X-ray source and the X-ray detector so as to exclude a portion of the imaging region where the object is present, wherein the processing unit is configured for selectively controlling the at least one beam restricting device upon generation of the warning signal.

6. The medical imaging system of claim 5, wherein the processing unit is configured for locating the object approaching the imaging region through identification of at least one proximity sensor of the plurality of proximity sensors for which a temporal difference exceeds the predetermined threshold.

7. The medical imaging system of claim 6, further comprising a warning provider, which is operable at least temporarily if a warning signal is generated by the processing unit.

8. The medical imaging system of claim 7, wherein the plurality of proximity sensors is further configured for acquiring distance information in a safety zone adjacent to the imaging region.

9. The medical imaging system of claim 1, wherein the processing unit is adapted for regenerating the reference distance information after a component of the X-ray image acquisition device and/or the patient support has been moved.

10. Method for preventing unintended X-ray radiation to an object in a medical imaging system, the method comprising:
generating X-ray beams through an X-ray source of an X-ray image acquisition device in direction of an X-ray detector of the X-ray image acquisition device, between which X-ray source and X-ray detector a patient support is positionable,
acquiring, from a plurality of proximity sensors located at, at least one of the X-ray source and the X-ray detector, distance information for an imaging region between the X-ray detector and the X-ray source,
generating reference distance information from distance information acquired without an object to be protected from unintended irradiation being present in the imaging region,
detecting a presence of said object in the imaging region by means of determining a temporal difference between actual distance information and the generated reference distance information and
generating a warning signal if the temporal difference exceeds a predetermined threshold being set outside a defined tolerance range representing boundary conditions for the distance information caused by patient movements.

11. The method of claim 10, further comprising interrupting the emission of X-ray radiation from the X-ray source if the warning signal is generated.

12. The method of claim 10, further comprising selectively controlling at least one beam restricting device upon generation of the warning signal to shape a field of irradiation between the X-ray source and the X-ray detector so as to exclude a portion of the imaging region where the object is present.

13. The method of claim 10, further comprising locating an object approaching into the field of irradiation by means of identifying at least one proximity sensor of the plurality of proximity sensors for which a temporal difference exceeds the predetermined threshold.

14. A non-transitory computer-readable medium storing program instructions which, when being executed by the processing unit- of a medical imaging system according to claim 1, causes the system to carry out a method for preventing unintended X-ray radiation to an object in a medical imaging system, the method comprising:
generating X-ray beams through the X-ray source of the X-ray image acquisition device in direction of the X-ray detector of the X-ray image acquisition device, between which X-ray source and X-ray detector a patient support is positionable,
acquiring, from a plurality of proximity sensors located at, at least one of the X-ray source and the X-ray detector, distance information for an imaging region between the X-ray detector and the X-ray source,
generating reference distance information from distance information acquired without an object to be protected from unintended irradiation being present in the imaging region,
detecting a presence of said object in the imaging region by means of determining a temporal difference between actual distance information and the generated reference distance information and
generating a warning signal if the temporal difference exceeds a predetermined threshold being set outside a defined tolerance range representing boundary conditions for the distance information caused by patient movements.

* * * * *